(12) United States Patent
Steinman et al.

(10) Patent No.: US 9,968,082 B2
(45) Date of Patent: May 15, 2018

(54) ORGAN TRANSPORTER WITH TILT AND/OR SHOCK SENSING

(71) Applicant: LIFELINE SCIENTIFIC, INC., Itasca, IL (US)

(72) Inventors: Christopher P. Steinman, Sandy, UT (US); John Stark, Bartlett, IL (US); Joel C. Hagen, Batavia, IL (US); Aaron R. Ferber, Chicago, IL (US); Rodney H. Monson, Waukegan, IL (US); Evan D. Shapiro, Chicago, IL (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 0 days. days.

(21) Appl. No.: 14/840,392

(22) Filed: Aug. 31, 2015

(65) Prior Publication Data

US 2015/0366183 A1    Dec. 24, 2015

Related U.S. Application Data

(62) Division of application No. 13/545,442, filed on Jul. 10, 2012, now Pat. No. 9,119,393.

(51) Int. Cl.
*A01N 1/02* (2006.01)

(52) U.S. Cl.
CPC .......... *A01N 1/0247* (2013.01); *A01N 1/0273* (2013.01)

(58) Field of Classification Search
CPC .......... A01N 1/00; A01N 1/02; A01N 1/0236; A01N 1/0242; A01N 1/0247; A01N 1/0263; A01N 1/0268; A01N 1/0273

USPC ............................................... 435/1.2, 248.1
See application file for complete search history.

(56) References Cited

U.S. PATENT DOCUMENTS

| | | | |
|---|---|---|---|
| 3,892,628 A * | 7/1975 | Thorne | A61M 1/32 435/1.2 |
| 5,217,860 A | 6/1993 | Fahy et al. | |
| 5,482,446 A * | 1/1996 | Williamson | A61M 5/142 417/234 |
| 5,551,850 A * | 9/1996 | Williamson | A61M 5/142 417/474 |
| 5,894,266 A | 4/1999 | Wood, Jr. et al. | |
| 6,074,180 A | 6/2000 | Khanwilkar et al. | |

(Continued)

FOREIGN PATENT DOCUMENTS

| | | |
|---|---|---|
| DE | 10 2010 015 040 A1 | 10/2011 |
| JP | H02-111101 A | 4/1990 |

(Continued)

OTHER PUBLICATIONS

Jan. 13, 2015 International Preliminary Report on Patentability issued in International Patent Application No. PCT/US2013/049593.

(Continued)

*Primary Examiner* — Lisa Caputo
*Assistant Examiner* — Philip Cotey
(74) *Attorney, Agent, or Firm* — Oliff PLC

(57) ABSTRACT

A method of perfusing an organ or tissue includes perfusing the organ or tissue with a perfusion apparatus; detecting a condition representing at least one of an attitude of the perfusion apparatus or at least one shock experienced by the perfusion apparatus; and altering perfusion based upon the detected condition and/or recording the detected condition.

12 Claims, 1 Drawing Sheet

(56) References Cited

U.S. PATENT DOCUMENTS

| | | | |
|---|---|---|---|
| 6,302,661 B1 | 10/2001 | Khanwilkar et al. | |
| 6,524,785 B1* | 2/2003 | Cozzone | A01N 1/02 |
| | | | 435/1.1 |
| 6,673,594 B1 | 1/2004 | Owen et al. | |
| 7,298,257 B2* | 11/2007 | Suzuki | A01N 1/02 |
| | | | 235/384 |
| 2003/0220609 A1* | 11/2003 | Childers | A61M 1/28 |
| | | | 604/29 |
| 2006/0100820 A1 | 5/2006 | Davidson | |
| 2006/0166360 A1* | 7/2006 | Berthiaume | A01N 1/02 |
| | | | 435/366 |
| 2006/0208881 A1* | 9/2006 | Suzuki | A01N 1/02 |
| | | | 340/539.27 |
| 2008/0145919 A1 | 6/2008 | Franklin et al. | |
| 2009/0029341 A1* | 1/2009 | Fuhr | A01N 1/00 |
| | | | 435/1.3 |
| 2010/0221830 A1 | 9/2010 | Sadler | |
| 2011/0076666 A1 | 3/2011 | Brassil | |
| 2011/0173023 A1 | 7/2011 | LeClair et al. | |
| 2012/0116152 A1 | 5/2012 | Faulkner et al. | |
| 2013/0267918 A1* | 10/2013 | Pan | A61M 1/0088 |
| | | | 604/318 |
| 2014/0017663 A1* | 1/2014 | Steinman | A01N 1/0247 |
| | | | 435/1.2 |

FOREIGN PATENT DOCUMENTS

| | | |
|---|---|---|
| JP | H02-124801 A | 5/1990 |
| JP | 2008515914 A | 5/2008 |
| WO | 2004/089085 A2 | 10/2004 |
| WO | 2006042138 A2 | 4/2006 |

OTHER PUBLICATIONS

Transportation: Commercial Benefits-Spinoff, retrieved from http://spinoff.nasa.gov/spinoff2000/t1.htm, retrieved Jul. 3, 2012, 1 page.

Shock and Vibration Data Logger, retrieved from http://en.wikipedia.org/wiki/Shock_and_vibration_data_logger, retrieved Jul. 3, 2012, pp. 1-9.

KIPP, "Understanding Today's Transportation Environment Measuring Recorders," ISA 44th International Instrument Symposium, 1998, pp. 1-13.

Jul. 8, 2013 European Search Report issued in International Application No. PCT/US2013/049593.

Jan. 31, 2017 Office Action issued in Japanese Patent Application 2015-521696.

\* cited by examiner

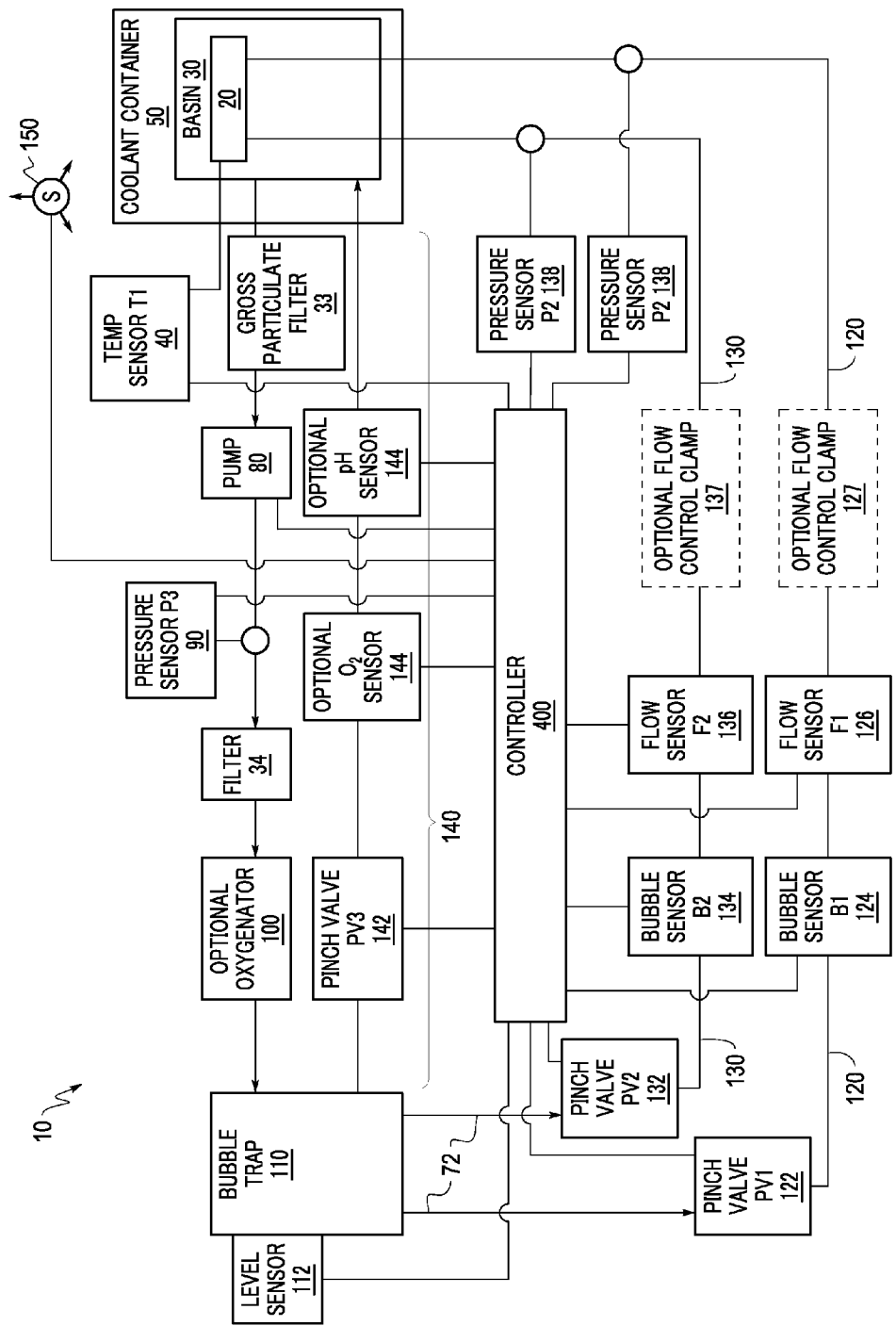

ORGAN TRANSPORTER WITH TILT AND/OR SHOCK SENSING

This application is a divisional application of U.S. patent application Ser. No. 13/545,442 filed Jul. 10, 2012, the entire disclosure of which is incorporated herein by reference.

BACKGROUND

Related technical fields include organ or tissue perfusion apparatuses that are capable of sustaining and/or restoring viability of organs or tissue and preserving organs or tissues for diagnosis, treatment, storage and/or transport. For convenience, the term "organ" as used herein should be understood to mean organ and/or tissue unless otherwise specified.

It is an objective of organ perfusion apparatus to mimic the conditions of the human body such that the organ remains viable before being used for research, diagnosis, treatment or transplantation. Many times the organ needs to be stored and/or transported between facilities. A goal of sustaining and restoring organs during perfusion is to reduce ischemia and reperfusion injury. The increase in storage periods in a normal or near normal functioning state also provides certain advantages, for example, organs can be transported greater distances and there is increased time for testing, treatment and evaluation of the organs.

In maintaining organs in near ideal conditions and physiological states it is known to provide a portable organ perfusion apparatus.

U.S. Pat. No. 6,673,594 discloses, for example, a configuration in which a portable organ perfusion apparatus is provided, which is hereby incorporated by reference in its entirety and in which the present invention could be used.

SUMMARY

When an organ has been harvested or engineered, it may be beneficial to transport and/or store the organ in a portable perfusion apparatus, and the organ may be transported over any distance. During such transportation, the apparatus may be subject to handling that could alter the attitude of the apparatus and/or subject the apparatus to shock. If the attitude of the apparatus exceeds a predetermined angle with respect to a normal operating attitude (e.g., horizontal), the device may perform sub-optimally or even fail. For example, if the attitude of the device deviates too far from a normal operating attitude, gas could be drawn into a perfusion circuit if an inlet to the perfusion circuit that is normally below a perfusate level is exposed to air or other gas. Similarly, components that are normally not exposed to perfusate could be exposed to perfusate if the apparatus is tilted too far, potentially causing failure or abnormal operation. If the device is subject to excessive physical shock (e.g., excessive g-force), the apparatus could suffer damage. Similarly, any organ contained in the apparatus could be damaged if the apparatus is subject to excessive shock. Accordingly, it is desirable to provide an organ perfusion apparatus with a shock and/or tilt detector. For example, an accelerometer can detect an orientation of the apparatus and/or shock to the apparatus. Preferably, the apparatus can alter its operation based upon a signal generated by the tilt and/or shock detector. The apparatus may permanently or temporarily cease perfusion if the attitude exceeds a predetermined angle or experiences one or more shocks above predetermined limits with respect to normal operation. The apparatus may record shocks and or changes in attitude, preferably if the shocks and/or changes in attitude exceed respective predetermined amounts.

BRIEF DESCRIPTION OF THE DRAWINGS

FIG. 1 is a schematic diagram of an organ perfusion apparatus.

DETAILED DESCRIPTION OF EMBODIMENTS

According to exemplary implementations, an apparatus is provided for perfusing an organ and sensing a tilt and/or a shock acting on the apparatus. The apparatus may include a perfusion circuit configured to perfuse the organ or tissue and one or more shock and/or tilt detectors. The apparatus may include a controller configured to control the apparatus based upon a signal received from the shock and/or tilt detector(s). The shock and/or tilt detector(s) may be configured to detect an angle of the apparatus with respect to a normal operational attitude of the apparatus. The controller may be configured to control the perfusion circuit based upon the angle. The controller may stop the perfusion circuit when the angle exceeds a predetermined angle. The controller may restart the perfusion circuit when the angle no longer exceeds the predetermined angle.

A shock detector such as an accelerometer may be configured to detect shocks experienced by the apparatus. The controller may be configured to record detected shocks detected by the accelerometer when the shocks exceed a predetermined threshold. A history of recorded shocks may be accessible by a user.

Exemplary implementations may include a method of perfusing an organ or tissue. The method may include perfusing the organ or tissue with a perfusion apparatus; detecting an attitude of the perfusion apparatus; and altering the perfusion based upon the detected attitude. The method may include stopping perfusion of the organ or tissue when the attitude of the apparatus exceeds a predetermined angle with respect to a normal attitude of operation. Perfusion of the organ or tissue may be resumed when the attitude of the apparatus no longer exceeds the predetermined angle.

Exemplary implementations may include a method of perfusing an organ or tissue including perfusing the organ or tissue with a perfusion apparatus; detecting a shock experienced by the perfusion apparatus; and recording the occurrence and, preferably, magnitude of the shock. Preferably, the shock is detected while perfusing the organ or tissue.

FIG. 1 is a schematic diagram of an exemplary perfusion apparatus 10 for an organ 20. The organ 20 may preferably be a liver, kidney, heart, lung or intestine, but may be any human or animal, natural or engineered, healthy, injured or diseased organ or tissue. The apparatus includes a basin 30 in which the organ may be placed. The basin 30 may hold a cradle on which the organ 20 is disposed when the organ 20 is in the apparatus 10. The basin 30 may include a first filter 33 that can function as a gross particulate filter. The basin 30 and/or the cradle are preferably configured to allow a perfusate bath to form around the organ 20. The basin 30 or apparatus 10 may also include a temperature sensor 40 located or focused in or near the cradle. The basin 30 or apparatus 10 may include multiple temperature sensors 40, which may provide redundancy in the event of a failure and/or may provide temperature measurement at multiple locations. Preferably, the temperature sensor(s) 40 is an infrared temperature sensor. The temperature sensor(s) 40 is preferably disposed as close as practical to the organ 20 when the organ 20 is disposed in the cradle in order to improve usefulness and accuracy of the temperature sensor(s) 40, which preferably provide a temperature measurement of the perfusate that may be correlated to a temperature of the organ 20. Alternatively or additionally, the temperature sensor(s) 40 may be used to directly measure the temperature of the organ 20.

The basin 30 is preferably disposed within a recess of an insulating coolant container 50 that may contain cold materials such as ice, ice water, brine or the like. Coolant container 50 may be permanently or removably attached to, or an integral, monolithic part of, apparatus 10. Thus, in use, the organ 20 is disposed within the cradle, which is disposed within the basin 30, which is disposed within the coolant container 50. The configuration of the coolant container 50, basin 30 and cradle preferably provides a configuration that provides cooling for the organ 20 without the contents of coolant container 50 contacting the organ 20 or the cradle. Although the coolant container 50 is described herein as containing ice or ice water, any suitable cooling medium can be used. Ice or ice water may be preferable due to the ease with which ice can procured, but one of ordinary skill would understand that any suitable cooling medium, which could be an active cooling medium (such as a thermo electric cooler or a refrigerant loop) or a passive cooling medium similar to ice or ice water, or a combination thereof, may be utilized. The amount of ice, or other cooling medium, that can be placed within the coolant container 50 should be determined based upon the maximum time that cooling is to be provided while the organ 20 will be in the apparatus 10.

The cradle may include components configured to securely restrain the organ 20 in place. Such components may, for example, include user selectable netting that is fastened to the cradle. The user selectable netting keeps the organ 20 in place while the organ 20 is manipulated or moved. For example, the organ may be held in place with the netting on the cradle while being manipulated (e.g., vasculature trimmed, cannulas attached, or the like) before being placed in the basin or perfusion apparatus. Similarly, the organ may be held in place when the organ 20 is moved with the cradle into the basin 30, when the basin 30 is moved into the coolant container 50 and when the apparatus 10 itself is moved during transport.

In the exemplary perfusion apparatus 10 of FIG. 1, after passing through the filter 33, the perfusate flows along a first flow path 70 that includes a suitable fluid conduit 72, such as flexible or rigid tubing, a pump 80, a pressure sensor 90, a second filter 34, an oxygenator 100 and a bubble trap 110, each of which is discussed below.

The first filter 33 is preferably a relatively coarse filter (relative to the second filter 34). Such a coarse filter may be provided to prevent large particles, which may for example be byproducts of the organ or of the organ being removed from the donor, from entering and clogging fluid paths of the apparatus 10. The first filter 33 may be an integral part of the basin 30 or the first filter 33 may be disposed elsewhere in the first flow path 70 downstream of the basin 30. For example, the first filter 33 may also be a separate component from the basin 30 or disposed within the fluid conduit 72.

The first flow path 70 may also include a pump 80. The pump 80 may be any pump that is suitable in connection with perfusing of organs. Examples of suitable pumps may include hand operated pumps, centrifugal pumps and roller pumps. If a roller pump is included, the roller pump may include a single channel or flow path (where only one tube is compressed by the rollers) or the roller pump may include multiple, parallel channels or flow paths (where multiple tubes are compressed by the rollers). If multiple, parallel channels or flow paths are included, the rollers may preferably be disposed out of phase or offset so that pulses created by the rollers are out of phase, which may result in a fluid flow out of the roller pump that is relatively less pulsatile than would be the case with a single roller. Such a multiple channel roller pump may achieve a constant flow rate or a minimally pulsatile flow rate, which may be advantageous depending on the other components in the flow path and/or the type of organ being perfused.

The flow path 70 may include a pressure sensor 90. The pressure sensor 90 may preferably be disposed after the outlet of the pump 80 in order to monitor and/or be used to control the pressure produced at the outlet of the pump by way of a suitable controller 400. The pressure sensor 90 may provide continuous or periodic monitoring of pressure.

The flow path 70 may include an oxygenator 100 such as an oxygenator membrane or body to provide oxygenation to the perfusate. Oxygen may be provided to the oxygenator 100 by any suitable means. Suitable oxygen sources may include pure oxygen or mixed gases such as air. The gas may be compressed, such as in a high-pressure cylinder, liquefied as would be stored in a dewar, or drawn from the surrounding atmosphere. Preferably, the oxygen may be provided by way of an oxygen generator, which may be separate from the apparatus 10 or integral to the apparatus 10. Oxygen may be generated through any suitable means, some examples of which include through pressure swing adsorption using a molecular sieve, through a ceramic oxygen generator (a solid state oxygen pump) or through decomposition of water.

The flow path 70 may include a bubble trap 110. The bubble trap 110 preferably separates gas bubbles that may be entrained in the perfusate flow and prevents such bubbles from continuing downstream and entering the organ 20. The bubble trap 110 may also function as an accumulator that reduces or eliminates pulsatility of the perfusate flow. The bubble trap 110 may include a volume of gas, initially or through the accumulation of bubbles, such that pressure fluctuations in the perfusate are dampened or eliminated.

The bubble trap 110 may include a vent that allows purging of gas during start up or a purging process. The vent may be connected to or part of purge flow path 140 (which is discussed in detail below). The vent is preferably open during a start up process so that any air or other gas may be purged from the perfusate path 70. Once the gas is purged from the perfusate path 70, the vent may preferably be closed. The vent may be closed manually or may be closed automatically by way of a controller 400.

The bubble trap 110 may include a level sensor 112. A level sensor 112 may optionally be used during the purging process to determine when the purging is complete and/or may be used to determine when the purging process needs to be repeated, which may happen after bubbles have been trapped in the bubble trap 110. Also, through the use of the level sensor 112 and the vent, the accumulator function of the bubble trap can be tuned to account for differing amplitudes and frequencies of pulsatility in the perfusate flow.

The bubble trap 110 may have any number of outlets, as needed for a given application of the perfusion apparatus. In FIG. 1, three outlets are shown connected to three different flow paths, which may be particularly suited for the perfusion of a liver. When perfusing a liver, the three paths preferably include portal flow path 120 connected to the portal vein of a liver, hepatic flow path 130 connected to the hepatic artery of a liver, and bypass flow path 140 that provides a return path to the basin 30. There may also be a port in any fluid path that allows fluid access to the perfusate solution. The port may preferably be located in the bubble trap 110. This port may preferably include a luer type fitting such that a user may extract a small a sample of the perfusate for analysis. The port may also be utilized by a user to administer substances to the perfusate without opening the basin.

As shown in FIG. 1, the portal flow path 120 and hepatic flow path 130 may optionally include similar or different components such as valves 122, 132; bubble sensors 124, 134; flow sensors 126, 136; flow control clamps 127, 137; and pressure sensors 128, 138. Each similar component may function in a similar manner, and such pairs of components may optionally be structurally and/or functionally identical to reduce manufacturing costs. Flow sensors 126, 136 may preferably be ultrasonic sensors disposed around tubing, although any suitable sensor may be used. Ultrasonic sensors may be advantageous because in normal usage such sensors do not come into contact with the perfusate and therefore are not in the sterile path. Such an implementation of ultrasonic sensors does not require replacement and/or cleaning after use.

Valves 122, 132 may be pinch valves that function to squeeze tubing and reduce or shut off flow, but any suitable valve may be used. Pinch valves may be advantageous because in normal usage they do not come into contact with the perfusate and therefore do not require replacement and/or cleaning after use.

Preferably, the bubble sensors 124; 134 are ultrasonic sensors disposed around tubing, although any suitable sensor may be used. Similar to pinch valves, ultrasonic sensors may be advantageous because in normal usage they do not come into contact with the perfusate and therefore do not require replacement and/or cleaning after use. Instead, ultrasonic sensors can be disposed in contact with, adjacent to or around an external surface of tubing in order to sense bubbles.

Flow control clamps 127, 137 may be used to fine-tune the flow rate in one or both of portal flow path 120 and hepatic flow path 130. Preferably, the organ provides self-regulation to control an amount of flow that exits the bubble trap 110 and is divided between the portal flow path 120 and the hepatic flow path 130. In such self regulated flow, pressure sensors 128, 138 provide overpressure monitoring. In the event that pressure delivered to the organ in either or both of the portal flow path 120 or the hepatic flow path 130 exceeds a predetermined threshold, the apparatus 10 can automatically stop and/or reduce the flow rate provided by the pump 80 to prevent damage to the organ. In addition or alternatively, the pressure sensors 128, 138 may be used to generate warning signals to the user and/or to an appropriate controller as pressures approach the predetermined threshold.

After exiting one or both of the portal flow path 120 and hepatic flow path 130, perfusate flows through the organ and returns to the basin 30 to form an organ bath.

Bypass flow path 140 may include a valve 142, and/or sensors such as oxygen sensor 144 and pH sensor 146. Preferably, the valve 142 is a pinch valve and may be of similar configuration to valves 122 and 132, but any suitable valve may be used. The oxygen sensor 144 and the pH sensor 146 may be used to determine the state of the perfusate. Preferably, the bypass flow path 140 is only used during a purging or priming process, although it may also be used during perfusion, preferably continuously, to monitor perfusate properties in real time.

The organ perfusion apparatus 10 may also include one or more shock and/or tilt detectors 150. An example of a combined such detector is an accelerometer. Preferably the accelerometer 150 is a three-axis accelerometer, although other multi-axis accelerometers or multiple single axis accelerometers may be used to the same effect. For example, complex digital 6-axis and 9-axis accelerometers or simple gravity-based, bubble-based, chemical reaction-based, or conductivity-based inclinometers or shock sensors could also be used. As would be understood by one of ordinary skill, any device capable of detecting, and preferably measuring, tilt and/or any device capable of detecting, and preferably measuring, shock may be used. The shock and/or tilt detector(s) 150 may be used to continuously or periodically monitor and/or record the state of the apparatus 10. Monitoring may include monitoring for excessive shocks as well as attitude of the apparatus 10. By implementing such monitoring, misuse or potentially inappropriate conditions of the apparatus 10 can be detected and recorded.

The controller 400 may utilize one or more signal generated by the shock and/or tilt detector(s) 150 to make decisions regarding controlling any components of the perfusion circuit, for example controlling the pump 80 and/or pinch valves 122, 132, 142. For example, if the accelerometer 150 generates a signal indicating that the attitude of the apparatus 10 has changed by more than a predetermined angle relative to a normal operating attitude or position, the controller 400 may generate a signal that stops the pump 80. Any components of the apparatus 10, in particular any components of the perfusion circuit, may be controlled based upon the predetermined angle. The controller 400 may close one or more of the pinch valves 132/142 to stop fluid, including liquid and/or gas, from flowing through the portal flow path 120, hepatic flow path 130, and/or any other flow path based upon the predetermined angle. The predetermined angle may be any angle selected according to the particular configuration of the apparatus. Preferably, the predetermined angle is between 5 and 25 degrees, more preferably between 5 and 10 degrees. For example, the predetermined angle could be 5 degrees, 10 degrees or any other angle between 5 and 25 degrees, inclusive, or more. The controller 400 may immediately change operation of the apparatus 10 when the attitude of the apparatus exceeds the predetermined angle, or the controller 400 may change operation of the apparatus 10 when the angle exceeds the predetermined angle for a predetermined of time. The predetermined time may be any period of time as determined by the configuration of the apparatus and/or needs of a user, which may be on the order of milliseconds, hundredths of a second, tenths of a second, seconds, or more. As would be understood by one of ordinary skill, the predetermined time may be determined from empirical testing or as dictated by a user such as a doctor or clinician. During perfusion, the controller 400 may slow down the pump 80, maintain the pump 80 at the same speed but shut the pinch valves 132/142, or slow down the pump 80 and shut the pinch valves 132/142 if the shock and/or tilt detector(s) 150 detects variation in tilt angles, which may occur at any angle, for example within 0 to 10 degrees of tilt. The controller 400 may stop the pump 80 and/or close the pinch valves 132/142 for short periods of time if any tilt is detected and restart the pump 80 and/or open the pinch valves 132/142 when tilt is no longer detected. The controller 400 may make similar decisions based upon shock or vibration levels exceeding a predetermined threshold.

The controller 400 may resume normal operation when the attitude of the apparatus 10 no longer exceeds the predetermined angle. For example, it may be preferable to resume operating the pump 80 to avoid damage to the organ, which may be caused if perfusion stops for too long. Alternatively, it may preferable not to resume perfusion if the apparatus 10 has tilted by more than a predetermined angle because, for example, the tilt may have allowed bubbles or other undesirable substances into the perfusate path and/or organ. It may be more preferable not to resume perfusion, but instead to maintain static cold storage, if the apparatus has tilted beyond the predetermined angle by more than a predetermined amount and/or for more than a predetermined period of time because the extended period of time may make it more likely that undesirable substances have entered the perfusate path and/or organ. Alternatively, a graduated control scheme may be utilized. For example, the controller 400 may slow the pump 80 if a first range of angles is detected (for example, greater than 0 but less than 5 degrees) and stop the pump 80 if a second range of angles is detected (for example, 5 to 10 degrees). If the second range of angles is maintained for more than a predetermined period of time, the controller 400 may cease perfusion and default to static cold storage. This predetermined time may be any time as determined by a user such as a doctor or clinician or based upon empirical testing, for example, 15 or 30 seconds, one minute, 5 minutes, or the like. If a third range of angles greater than the second range of angles (for example, greater than 10 degrees) is detected, the controller 400 may immediately default to static cold storage.

The controller 400 may record shocks sensed by the shock and/or tilt detector(s) 150. Recording shocks may be beneficial to provide an indication of whether the apparatus has been mishandled. Excessive shock(s) may cause damage to the organ and/or the apparatus 10. Thus, it may be preferable to record all shocks and/or shocks that exceed a predetermined threshold. The predetermined threshold may be determined based upon a shock that is of sufficient magnitude to damage the apparatus 10 and/or the organ. It may be preferable for the predetermined threshold to be below a level that will damage an organ. For example, the predetermined threshold may be in the range of 2 G to 3 G. A warning that an upper limit for shock was exceeded may generate a warning to the user. The controller may also sum shocks that occur, and this sum may be used to determine if the sum of shocks may have caused damage to the apparatus 10 and/or the organ. A record of shocks may be accessible by a user. A record of shocks may be displayed to notify a user of the shock(s), and/or the recorded shocks may not be displayed or may be displayed only upon entry of a passcode. Not openly displaying the shocks may be beneficial so that a manufacturer or maintenance provider can determine if a user has mishandled or misused the apparatus 10 but failed to inform the manufacturer or maintenance provider. Displaying the recorded shocks may be beneficial so that a user can take immediate action to repair any damage that may have occurred to the organ and/or the apparatus 10. The apparatus 10 may record shocks based upon a first threshold for shocks that will not be displayed and record shocks based upon a second threshold for shocks that will be displayed. Similarly, attitude of the apparatus 10 can be recorded and/or displayed openly or selectively. Preferably, recorded tilts and/or shocks can be accessible remotely. For example, the recorded tilts and/or shocks may be accessible over any network (such as a cellular network, a local wireless network, and/or the internet) that may be wired or wireless.

The apparatus 10 may include storage compartments for items other than the organ 20. For example, the apparatus 10 may include a document compartment to store documents and/or charts related to the organ 20. Also, the apparatus 10 may include one or more sample compartment. The sample compartment may be configured, for example, to store fluid and/or tissue samples. The sample compartment may be advantageously disposed near the coolant container 50 to provide cooling, which may be similar or equivalent to the cooling provided for the organ 20.

The apparatus 10 may include one or more tamper evident closures. A tamper evident closure may be used to alert a user that the apparatus 10 has been opened at an unauthorized time and/or location and/or by an unauthorized person. Evidence of tampering may alert the user to perform additional testing, screening, or the like before using the organ 20 and/or the apparatus 10. The apparatus 10 may include one or more tamper evident closures to provide evidence of tampering with the accelerometer 150 or associated records.

What has been described and illustrated herein are preferred embodiments of the invention along with some variations. The terms, descriptions and figures used herein are set forth by way of illustration only and are not meant as limitations. Those skilled in the art will recognize that many variations are possible within the spirit and scope of the invention.

What is claimed is:

1. A method of perfusing an organ or tissue, comprising:
   perfusing the organ or tissue with a perfusion apparatus;
   detecting an attitude of the perfusion apparatus;
   measuring a duration that the attitude of the perfusion apparatus exceeds a predetermined angle measured from a normal attitude of operation; and
   altering perfusion based upon the detected attitude and the measured duration.

2. The method according to claim 1, wherein the attitude of the apparatus is detected automatically by the perfusion apparatus.

3. The method according to claim 1, wherein altering perfusion comprises stopping perfusion of the organ or tissue when the attitude of the apparatus exceeds the predetermined angle with respect to the normal attitude of operation of the perfusion apparatus.

4. The method according to claim 3, wherein altering perfusion further comprises resuming perfusion of the organ or tissue when the attitude of the apparatus no longer exceeds the predetermined angle.

5. The method according to claim 1, further comprising recording occurrences of the detected attitude exceeding a predetermined variance from the normal attitude of operation of the perfusion apparatus.

6. The method according to claim 1, further comprising detecting and recording at least one shock experienced by the perfusion apparatus.

7. The method according to claim 1, wherein the method further comprises:
   detecting at least one shock experienced by the perfusion apparatus; and
   recording the shock in the perfusion apparatus.

8. The method according to claim 7, wherein the shock is detected by the perfusion apparatus while perfusing the organ or tissue.

9. The method according to claim 8, further comprising:
   detecting and measuring the magnitude of a plurality of shocks; and
   recording a processed indication of the total number and magnitude of the shocks in the apparatus.

10. The method according to claim 7, further comprising measuring the magnitude of the shock.

11. The method according to claim 1, wherein altering perfusion comprises slowing perfusion of the organ or tissue when the attitude of the apparatus exceeds the predetermined angle with respect to the normal attitude of operation of the perfusion apparatus.

12. The method according to claim 1, wherein altering perfusion comprises reducing perfusion of the organ or tissue when the duration exceeds a predetermined period of time.

* * * * *